United States Patent [19]
Bissett

[11] Patent Number: 5,962,482
[45] Date of Patent: Oct. 5, 1999

[54] METHOD OF REDUCING CELLULITE IN MAMALIAN SKIN

[75] Inventor: Donald Lynn Bissett, Hamilton, Ohio

[73] Assignee: The Procter & Gamble Company, Cincinnati, Ohio

[21] Appl. No.: 09/267,264

[22] Filed: Mar. 12, 1999

Related U.S. Application Data

[60] Provisional application No. 60/078,163, Mar. 16, 1998.

[51] Int. Cl.⁶ .................................................. A61K 31/44
[52] U.S. Cl. ............................................................ 514/356
[58] Field of Search ............................................... 514/356

[56] References Cited

U.S. PATENT DOCUMENTS

| | | | |
|---|---|---|---|
| 4,086,922 | 5/1978 | Henderson | 601/125 |
| 4,829,987 | 5/1989 | Stewart | 424/154 |
| 5,514,374 | 5/1996 | Bonte et al. | 424/195.1 |
| 5,536,499 | 7/1996 | Znaiden et al. | 424/401 |
| 5,591,437 | 1/1997 | Bonte et al. | 424/195.1 |
| 5,658,576 | 8/1997 | Soudant | 514/356 |
| 5,705,170 | 1/1998 | Kong et al. | 424/401 |

FOREIGN PATENT DOCUMENTS

| | | | |
|---|---|---|---|
| 73-2222008 | 10/1974 | France | A61K 27/00 |
| 4401308 A1 | 7/1995 | Germany | A61K 7/48 |

OTHER PUBLICATIONS

"Preparations and applications of nicotinic acid and nicotinamide", Chimica OGGI/Chemistry Today, 14 (6), 55–57, Jun. 1996.

*Federal Register*, vol. 56, No. 153/Thursday, Aug. 8, 1991/ Rules and Regulations, Dept. of Health and Human Services, FDA, 21 CFR Part 310, 37792–27799.

U.S. application No. 09/267,814, Attorney Docket No. 7056, filed Mar. 12, 1999.

U.S. application No. 09/267,815, Attorney Docket No. 7057, filed Mar. 12, 1999.

U.S. application No. 09/267,817, Attorney Docket No. 7058, filed Mar. 12, 1999.

U.S. application No. 09/267,816, Attorney Docket No. 7059, filed Mar. 12, 1999.

U.S. application No. 09/267,851, Attorney Docket No. 7060, filed Mar. 12, 1999.

U.S. application No. 09/267,852, Attorney Docket No. 7063M, filed Mar. 12, 1999.

U.S. application No. 09/267,849, Attorney Docket No. 7064M, filed Mar. 12, 1999.

U.S. application No. 09/267,874, Attorney Docket No. 7455, filed Mar. 12, 1999.

*Primary Examiner*—Raymond Henley, III
*Attorney, Agent, or Firm*—Darryl C. Little

[57] ABSTRACT

The present invention relates to a method for combating cellulite or reducing localized fatty excesses which comprises administering to a person having cellulite or localized fatty excesses a body slimming amount of a composition containing niacinamide.

9 Claims, No Drawings

METHOD OF REDUCING CELLULITE IN MAMALIAN SKIN

CROSS REFERENCE

This application claims priority under Title 35, United States Code 119(e) from Provisional Application Serial No. 60/078,163, filed Mar. 16, 1998.

FIELD OF THE INVENTION

The present invention relates to a method for combating cellulite or reducing localized fatty excesses which comprises administering to a person having cellulite or localized fatty excesses a body slimming amount of a composition containing niacinamide.

BACKGROUND OF THE INVENTION

Cellulite afflictions are a stubborn problem causing emotional and psychological distress to many women. Cellulite primarily afflicts the thighs and buttocks but may also be present on the stomach and upper arms. Frequently, cellulite presents an unsightly, lumpy orange-peel appearance. Clinically, cellulite manifests a range of symptoms including thinning of the epidermis, reduction and breakdown of the microvasculature leading to subdermal accumulations of fluids, and subdermal agglomerations of fatty tissue. It has been observed that polymeric proteoglycans are a primary component of these agglomerations.

To liberate these trapped fatty agglomerations and fluids, the local application of enzymes or enzyme containing compositions has been proposed since the enzymes are capable of depolymerizing the proteoglycans. These enzymes include mucopolysaccharidases and, more particularly, hyaluronidase, thiomucase and α-mucase.

Among the methods for stimulating lipolysis, the most commonly known and used is that which consists in inhibiting the phosphodiesterase in order to prevent or at least limit the rate of degradation of cyclic AMP. In effect, the phosphodiesterase destroys cyclic AMP by transforming it into 5' AMP so that it cannot function as a lipolysis activator.

It is important then to inhibit the activity of the phosphodiesterase in a manner so as to have a high amount of cyclic AMP at the level of the adipocytes thereby stimulating lipolytic activity.

Representative various phosphodiesterase inhibitors, which have been known as slimming agents, include in particular xanthine derivatives and more particularly theophylline, caffeine and theobromine.

Moreover, it has also been known to use certain oleo-soluble vegetable extracts which, according to a different mechanism, can also act as a slimming agent. For instance, in U.S. Pat. No. 4,795,638 there is disclosed a thermo slimming cosmetic composition containing an oil-soluble plant extract having slimming action. Representative of these oil-soluble plant extracts are vegetable extracts including, principally, those of climbing ivy (*Hedera helix*), arnica (*Arnica montana*), rosemary (*Rosmarinus officinalis* N), marigold (*Calendula officinalis*), sage (*Salvia officinalis* N), ginseng (*Panax ginseng*), St. Johns-wart (*Hypericum perforatum*), ruscus (*Ruscus aculeatus*), meadowsweet (*Filipendula ulmaria* L) and orthosiphon (*Ortosifon stamincus* Benth), as well as mixtures of these vegetable extracts.

Notwithstanding such disclosures, there remains a need for improved compositions for reducing cellulite in mammalian skin. The present inventor has found that skin care compositions containing niacinamide aid in reducing cellulite in skin.

Accordingly, it is an object of the present invention to provide methods for reducing cellulite in mammalian skin.

It is also an object of the present invention to provide topically applied, skin compositions for reducing cellulite containing a safe and effective amount of niacinamide.

These and other objects will become readily apparent from the detailed description which follows.

SUMMARY OF THE INVENTION

The present invention relates to methods treating and/or preventing cellulite by administering a safe and effective amount of a skin care composition comprising:

a). a safe and effective amount of niacinamide; and b). a dermatologically acceptable carrier for the niacinamide.

The present invention further relates to articles of manufacture comprising a skin care composition comprising from about 0.1% to about 40%, by weight, niacinamide in a package for said skin care composition in association with the information about and/or instructions on the use of niacinamide to treat cellulite.

Unless otherwise indicated, all percentages and ratios used herein are by weight of the total composition. All weight percentages, unless otherwise indicated, are on an actives weight basis. All measurements made are at approximately 25° C., unless otherwise designated. The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan.

DETAILED DESCRIPTION OF THE INVENTION

The compositions used in the present invention can comprise, consist of, or consist essentially of the essential elements and limitations of the invention described herein, as well any of the additional or optional ingredients, components, or limitations described herein.

Essential Components

Niacinamide

Nicotinic acid and niacinamide (nicotinamide or nicotinic acid amide) are water soluble vitamins, whose physiologically active forms nicotinamide adenine dinucleotide (NAD) and nicotinamide adenine dinucleotide phosphate (NADP) serve a vital role as coenzymes in a variety of important metabolic reactions. Nicotinic acid is an essential dietary constituent, the lack of which leads to pellagra, a condition characterized by an erythematous skin eruption as well as gastrointestinal and neurological symptoms. Nicotinic acid and niacinamide have been used routinely to treat pellagra for which they are therapeutic.

Nicotinic acid as well as niacinamide are available from a variety of pharmaceutical houses such as Armor Pharmaceutical Company located in Phoenix, Ariz.; Brown Pharmaceutical Company Inc. located in Los Angeles, Calif.; and Keith Pharmaceutical Inc. located in Miami, Fla.

Without being bound by theory, niacinamide is believed to reduce cellulite by several mechanisms. Niacinamide stimulates epidermal cells and thus would thicken the tissue to overcome the thinning of the epidermis that is associated with cellulite. These compounds are also vasoactive (stimulate blood flow) and thus would improve the reduction in microvascularization associated with cellulite. Additionally, niacinamide stimulates metabolism in skin cells in general (e.g., epidermis, dermis, subcutaneous fat) which would increase cellular production of the enzymes for turnover or removal of the agglomerations of fatty tissue and/or proteoglycans.

Niacinamide is preferably present in the compositions used in the present invention at concentrations of from about 0.1% to about 50%, more preferably from about 1% to about 30%, and still more preferably from about 1% to about 20%, most preferably from above 1% to about 10%.

Carrier

The compositions used in the present invention also contain a dermatologically acceptable carrier. The phrase "dermatologically-acceptable carrier", as used herein, means that the carrier is suitable for topical application to the skin, has good aesthetic properties, is compatible with the actives of the present invention and any other components, and will not cause any untoward safety or toxicity concerns. A safe and effective amount of carrier is from about 50% to about 99.99%, preferably from about 99.9% to about 80%, more preferably from about 98% to about 90%, most preferably from about 95% to 90% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" *Cosmetics & Toiletries*, vol. 105, pp. 122–139 (December 1990); "Sun Products Formulary", *Cosmetics & Toiletries*, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers of the skin care compositions can comprise from about 50% to about 99% by weight of the compositions used in the present invention, preferably from about 75% to about 99%, and most preferably from about 85% to about 95%.

Preferred cosmetically and/or pharmaceutically acceptable topical carriers include hydroalcoholic systems and oil-in-water emulsions. When the carrier is a hydro-alcoholic system, the carrier can comprise from about 0% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. A more detailed discussion of suitable carriers is fount in U.S. Pat. No. 5,605,894 to Blank et al., and in PCT application WO 97/39733, published Oct. 30, 1997, to Oblong et al., both herein incorporated by reference in their entirety.

Optional Components

The compositions used in the present invention may optionally comprise additional materials including slimming agents as well as additional actives useful in providing cellulite control. Among these agents are phosphodiesterase inhibitors (e.g., xanthine derivatives such as theophylline, caffeine, theobromine or salts thereof such as aminophylline) and certain oleosoluble vegetable extracts, including, principally, those of climbing ivy (*Hedera helix*), arnica (*Arnica montana*), rosemary (*Rosmarinus officinalis* N), marigold (*Calendula officinalis*), sage (*Salvia officinalis* N), ginseng (*Panax ginseng*), St. Johns-wart (*Hypericum perforatum*), ruscus (*Ruscus aculeatus*), meadowsweet (*Filipendula ulmaria* L) and orthosiphon (*Ortosifon stamincus* Benth), as well as mixtures of these vegetable extracts, all of which are disclosed in U.S. Pat. No. 4,795,638, herein incorporated by reference.

Also useful are herbal and/or botannical extracts such as those disclosed in U.S. Pat. Nos. 5,705,170 and 5,667,793, both of which are herein incorporated by reference. Mixtures of any of above additional materials may also be used. The compositions used in the present invention may optionally comprise additional skin actives. Non-limiting examples of such skin actives include hydroxy acids such as salicylic acid; desquamatory agents such as zwitterionic surfactants; sunscreens such as 2-ethylhexyl-p-methoxycinnamate, 4,4'-t-butyl methoxydibenzoyl-methane, octocrylene, phenyl benzimidazole sulfonic acid; sun-blocks such as zinc oxide and titanium dioxide; anti-inflammatory agents; corticosteroids such as hydrocortisone, methylprednisolone, dexamethasone, triamcinolone acetconide, and desoxametasone; anesthetics such as benzocaine, dyclonine, lidocaine and tetracaine; antipruitics such as camphor, menthol, oatmeal (colloidal), pramoxine, benzyl alcohol, phenol and resorcinol; anti-oxidants/radical scavengers such as tocopherol and esters thereof; chelators; retinoids such as retinol, retinyl palmitate, retinyl acetate, retinyl propionate, and retinal; hydroxy acids such as glycolic acid; keto acids such as pyruvic acid; N-acetyl-L-cysteine and derivatives thereof; benzofuran derivatives; and skin protectants. Mixtures of any of the above mentioned skin actives may also be used. A more detailed description of these actives is found in U.S. Pat. No. 5,605,894 to Blank et al. (previously incorporated by reference). Preferred skin actives include hydroxy acids such as salicylic acid, sunscreen, antioxidants and mixtures thereof.

Other conventional skin care product additives may also be included in the compositions used in the present invention. For example, urea, guanidine, glycerol, petrolatum, mineral oil, sugar esters and polyesters, polyolefins, methyl isostearate, ethyl isostearate, cetyl ricinoleate, isononyl isononanoate, isohexadecane, lanolin, lanolin esters, cholesterol, pyrrolidone carboxylic acid/salt (PCA), trimethyl glycine (betaine), tranexamic acid, amino acids (e.g., serine, alanine), panthenol and its derivatives, collagen, hyaluronic acid, elastin, hydrolysates, primrose oil, jojoba oil, epidermal growth factor, soybean saponins, mucopolysaccharides, and mixtures thereof may be used. Other suitable additives or skin actives are discussed in further detail in PCT application WO 97/39733, published Oct. 30, 1997, to Oblong et al., herein incorporated by reference in its entirety.

Preparation of Skin Care Compositions

The compositions used in the present invention are generally prepared by conventional methods such as are known in the art of making topical compositions. Such methods typically involve mixing of the ingredients in one or more steps to a relatively uniform state, with or without heating, cooling, application of vacuum, and the like. Non-limiting examples of the product form can be a gel, emulsion, lotion, cream, ointment, solution, liquid, etc.

Methods for Treating Cellulite

The methods of the present invention are useful for especially preventing cellulite, especially in the subcutaneous, dermis and epidermis tissues of mammalian skin. The methods of the present invention involve topically applying to the skin and effective amount of the skin care composition of the present invention. The amount of the composition which is applied, the frequency of application and the period of use will vary widely depending upon the level of niacinamide and/or other components of a given composition and the degree of cellulite fading desired.

The skin care compositions used in the present invention can be chronically applied to the skin. By "chronic topical application" is meant continued topical application of the composition over an extended period during the subject's lifetime, preferably for a period of at least about one week, more preferably for a period of at least about two weeks, even more preferably for a period of at least one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime to maintain and/or increase the benefits achieved. Typically applications would be on the order of one to four times per day over such extended periods, however application rates can be more than four times per day, especially on areas particularly prone to agglomerations of fat and water such as the thighs and buttocks.

A wide range of quantities of the compositions used in the present invention can be employed to provide a skin appearance and/or feel benefit. Quantities of the present compositions which are typically applied per application are, in mg composition/$cm^2$ skin, from about 0.1 mg/$cm^2$ to about 10 mg/$cm^2$. A particularly useful application amount is about 2 mg/$cm^2$.

The method of treating cellulite is preferably practiced by applying a composition in the form of a skin lotion, cream, gel, cosmetic, or the like which is intended to be left on the skin for some aesthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, most preferably for at least several hours, e.g., up to about 12 hours.

Another approach to ensure a continuous exposure of the skin to at least a minimum level niacinamide is to apply the compound by use of a patch. Such an approach is particularly useful for problem skin areas needing more intensive treatment. The patch can be occlusive, semi-occlusive or non-occlusive. The niacinamide composition can be contained within the patch or be applied to the skin prior to application of the patch. The patch can also include additional actives such as chemical initiators for exothermic reactions such as those described in PCT application WO 9701313 to Burkett et al. Preferably the patch is applied at night as a form of night therapy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

The following is an example of a skin cream incorporating the compositions of the present invention. The compositions are formed by combining and mixing the ingredients of each column using conventional technology and then applying to the skin from about 0.5 g to about 50 g.

| Ingredient | % Weight |
| --- | --- |
| Glycerine | 6.933 |
| Niacinamide | 15.000 |
| Permethyl 101A[1] | 3.000 |
| Sepigel[2] | 2.500 |
| Q2-1403[3] | 2.000 |
| Isopropyl Isostearate | 1.330 |
| Arlatone 2121[4] | 1.000 |
| Cetyl Alcohol CO-1695 | 0.720 |
| SEFA Cottonate[5] | 0.670 |
| Tocopherol Acetate | 0.500 |
| Panthenol | 0.500 |
| Adol 62[6] | 0.480 |
| Kobo Titanium Dioxide | 0.400 |
| Sodium Hydroxide 50% Aqueous | 0.0125 |
| Fiery 5[7] | 0.150 |
| Disodium EDTA | 0.100 |
| Glydant Plus[8] | 0.100 |
| Myrj 59[9] | 0.100 |
| Emersol 132[10] | 0.100 |
| Color | 0.00165 |
| Purified Water | q.s. to 100 |

Example 2

The following is an example of a skin cream incorporating the compositions of the present invention. The compositions are formed by combining and mixing the ingredients of each column using conventional technology and then applying to the skin from about 0.5 g to about 50 g.

| Ingredient | % Weight |
| --- | --- |
| Glycerine | 6.933 |
| Niacinamide | 12.000 |
| Permethyl 101A[1] | 3.000 |
| Sepigel[2] | 2.500 |
| Q2-1403[3] | 2.000 |
| Isopropyl Isostearate | 1.330 |
| Arlatone 2121[4] | 1.000 |
| Cetyl Alcohol CO-1695 | 0.720 |
| SEFA Cottonate[5] | 0.670 |
| Tocopherol Acetate | 0.500 |
| Panthenol | 0.500 |
| Adol 62[6] | 0.480 |

-continued

| Ingredient | % Weight |
| --- | --- |
| Kobo Titanium Dioxide | 0.400 |
| Sodium Hydroxide 50% Aqueous | 0.0125 |
| Fiery 5[7] | 0.150 |
| Disodium EDTA | 0.100 |
| Glydant Plus[8] | 0.100 |
| Myrj 59[9] | 0.100 |
| Emersol 132[10] | 0.100 |
| Color | 0.00165 |
| Purified Water | q.s. to 100 |

Example 3

The following is an example of a skin cream incorporating the compositions of the present invention. The compositions are formed by combining and mixing the ingredients of each column using conventional technology and then applying to the skin from about 0.5 g to about 50 g.

| Ingredient | % Weight |
| --- | --- |
| Glycerine | 6.933 |
| Niacinamide | 12.000 |
| Permethyl 101A[1] | 4.000 |
| Q2-1403[3] | 2.000 |
| Isopropyl Isostearate | 1.330 |
| Arlatone 2121[4] | 1.000 |
| Cetyl alcohol CO-1695 | 0.720 |
| SEFA Cottonate[5] | 0.670 |
| Carbopol 954[11] | 0.500 |
| Tocopherol Acetate | 0.500 |
| Panthenol | 0.500 |
| Adol 62[6] | 0.480 |
| Kobo Titanium Dioxide | 0.400 |
| Sodium Hydroxide 50% Aqueous | 0.250 |
| Fiery 5[7] | 0.150 |
| Disodium EDTA | 0.100 |
| Glydant Plus[8] | 0.100 |
| Myrj 59[9] | 0.100 |
| Emersol 132[10] | 0.100 |
| Carbopol 1382[12] | 0.100 |
| Color | 0.00165 |
| Purified Water | q.s. to 100 |

[1]Isohexadecane, Presperse Inc., South Plainfield, NJ
[2]Polyacrylamide(and)C13-14 Isoparaffin(and)Laureth-7, Seppic Corporation, Fairfield, NJ
[3]dimethicone(and)dimethiconol, Dow Corning Corp., Midland, MI
[4]Sorbitan Monostearate and Sucrococoate, ICI Americas Inc., Wilmington, DE
[5]Sucrose ester of fatty acid, Procter and Gamble, Cincinnati, OH
[6]Stearyl alcohol, Procter and Gamble, Cincinnati, OH
[7]Fiery 5 n/a, Procter and Gamble, Cincinnati, OH
[8]DMDM Hydantoin (and) Iodopropynyl Butylcarbamate, Lonza Inc., Fairlawn, NJ
[9]PEG-100 Stearate, ICI Americas Inc., Wilmington, DE
[10]Stearic acid, Henkel Corp., Kankakee, IL
[11]Carbomer, BF Goodrich, Cleveland OH
[12]Carbomer, BF Goodrich, Cleveland OH

What is claimed is:

1. A method of treating and/or preventing cellulite by administering a safe and effective amount of a skin care composition to a mammal having, or prone to forming cellulite, comprising:
    a). a safe and effective amount of niacinamide; and
    b). a dermatologically acceptable carrier for the niacinamide.

2. A method according to claim 1, wherein the concentration of niacinamide from about 1% to about 20%.

3. A method according to claim 1, wherein the niacinamide is substantially uncomplexed.

4. A method according to claim 1, wherein the composition further comprises an additional active selected from the group consisting of phosphodiesterase inhibitors, oleo-soluble vegetable extracts, herbal extracts, botannical extracts and mixtures thereof.

5. A method according to claim 4, wherein the additional active is a phosphodiesterase inhibitor selected from the group consisting of theophylline, caffeine, theobromine, salts thereof and mixtures thereof.

6. A method according to claim 1, wherein the composition further comprises an additional skin active selected from the group consisting of hydroxy acids, desquamatory agents, sunscreens, anti-oxidants, retinoids and mixtures thereof.

7. A method according to claim 6, wherein the hydroxy acid is salicylic acid; the desquamatory agent is selected from the group consisting of zwitterionic surfactants and mixtures thereof; the sun-block is selected from the group consisting of zinc oxide, titanium dioxide and mixtures thereof; the sunscreen is selected from the group consisting of 2-ethylhexyl-p-methoxycinnamate, 4,4'-t-butyl methoxydibenzoyl-methane, phenyl benzimidazole sulfonic acid, octocrylene and mixtures thereof; the anti-oxidant is selected from the group consisting of tocopherol, esters thereof and mixtures thereof; and the retinoid is selected from the group consisting of retinol, retinyl acetate, retinyl propionate, and mixtures thereof.

8. A method according to claim 1, wherein the skin care composition is contained within a patch or is applied to the skin and covered by a patch.

9. An article of manufacture comprising a skin care composition comprising from about 0.1% to about 40%, by weight, niacinamide in a package for said skin care composition in association with the information about and/or instructions on the use of niacinamide to treat cellulite.

* * * * *

UNITED STATES PATENT AND TRADEMARK OFFICE
CERTIFICATE OF CORRECTION

PATENT NO.    :    5,962,482

DATED         :    October 5, 1999

INVENTOR(S)   :    Donald Lynn Bissett

It is certified that error appears in the above-identified patent and that said Letters Patent is hereby corrected as shown below:

On the title page, item [54] and column 1, line 2 "Mamalian" should read --Mammalian--.
At column 5, line 18 "especially preventing" should read --treating or preventing--.

Signed and Sealed this

Twentieth Day of June, 2000

Attest:

Q. TODD DICKINSON

*Attesting Officer*                *Director of Patents and Trademarks*